United States Patent [19]

Erickson et al.

[11] Patent Number: 5,755,695
[45] Date of Patent: May 26, 1998

[54] GUIDEWIRE STEERING HANDLE AND METHOD OF USING SAME

[75] Inventors: David S. Erickson, Stillwater, Minn.; Andrew Feiring, Milwaukee, Wis.

[73] Assignee: Microvena Corporation, White Bear Lake, Minn.

[21] Appl. No.: 439,408

[22] Filed: May 11, 1995

[51] Int. Cl.$^6$ .................................................. A61M 5/178
[52] U.S. Cl. ............................................ 604/164; 604/905
[58] Field of Search ............................ 604/164, 178, 604/95, 104, 174, 165, 166, 96, 305; 128/772

[56] References Cited

U.S. PATENT DOCUMENTS

| | | |
|---|---|---|
| 3,199,549 | 8/1965 | Wallshein . |
| 3,229,727 | 1/1966 | Kenlon . |
| 4,184,259 | 1/1980 | Sosnay . |
| 4,716,757 | 1/1988 | McGregor et al. . |
| 4,858,810 | 8/1989 | Intlekofer et al. . |
| 4,957,117 | 9/1990 | Wysham ............................ 128/772 |
| 4,964,854 | 10/1990 | Luther ............................... 604/166 |
| 4,966,586 | 10/1990 | Vaillancourt ...................... 604/164 |
| 5,110,291 | 5/1992 | Randin . |
| 5,186,712 | 2/1993 | Kelso et al. ...................... 604/164 |
| 5,190,050 | 3/1993 | Nitzsche ........................... 604/164 |
| 5,217,435 | 6/1993 | Kring ................................ 128/772 |
| 5,277,231 | 1/1994 | Dostalek . |
| 5,325,746 | 7/1994 | Anderson ......................... 128/772 |
| 5,527,292 | 6/1996 | Adams et al. .................... 128/772 |

OTHER PUBLICATIONS

Page from catalog by SCIMED Life Systems, Inc., ©1990.
Pages from catalog by Medi•Tech, Boston Scientific Corporation, ©1993.
Brochure entitled "Probe III, Ballon–on–a–Wire Dilatation System", USCI, C.R. Bard, Inc., 1991.
Article by Heeney, "Shape Your Guide Wire", Aug. 1983, American Journal of Roentgenology, pp. 405–406.
Article by Stocker, "Simple Technique for Shaping Hydrophilically Coated Guide Wires: Usefulness in Selective Angiography", Dec. 1990, Journal of Radiology, vol. 177, No. 3, pp. 881–882.

*Primary Examiner*—Robert A. Hafer
*Assistant Examiner*—Justine R. Yu
*Attorney, Agent, or Firm*—Fredrikson & Byron, PA

[57] ABSTRACT

A steering handle for guiding a medical guidewire and a catheter through a patient's vessels to a treatment site and a method of using the steering handle. The steering handle may be selectively converted to guide the guidewire and catheter either independently or together as a fixed unit. Additionally, a shaping device may be provided on the steering handle which a physician may use to shape a distal segment of the guidewire into a desired shape with ease and accuracy.

6 Claims, 4 Drawing Sheets

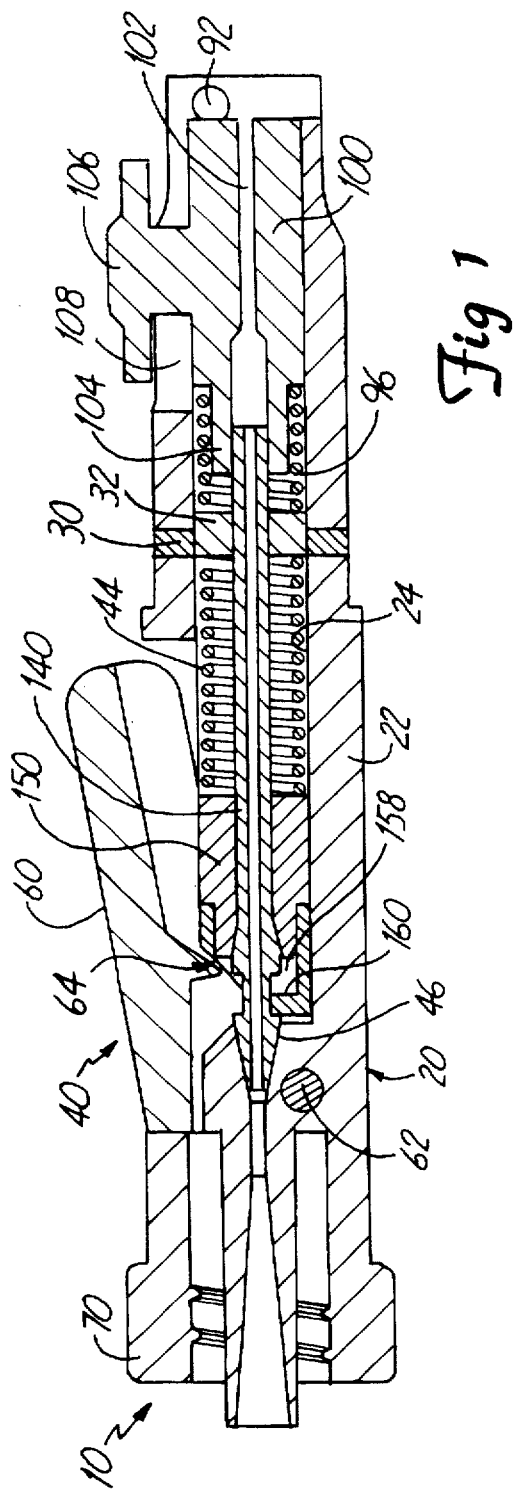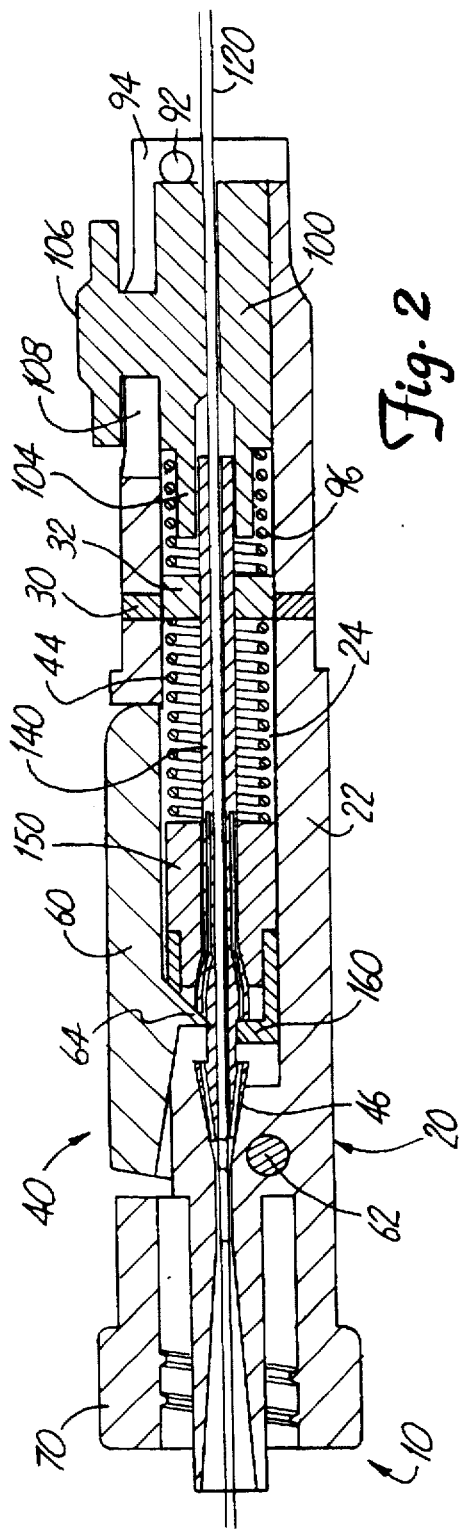

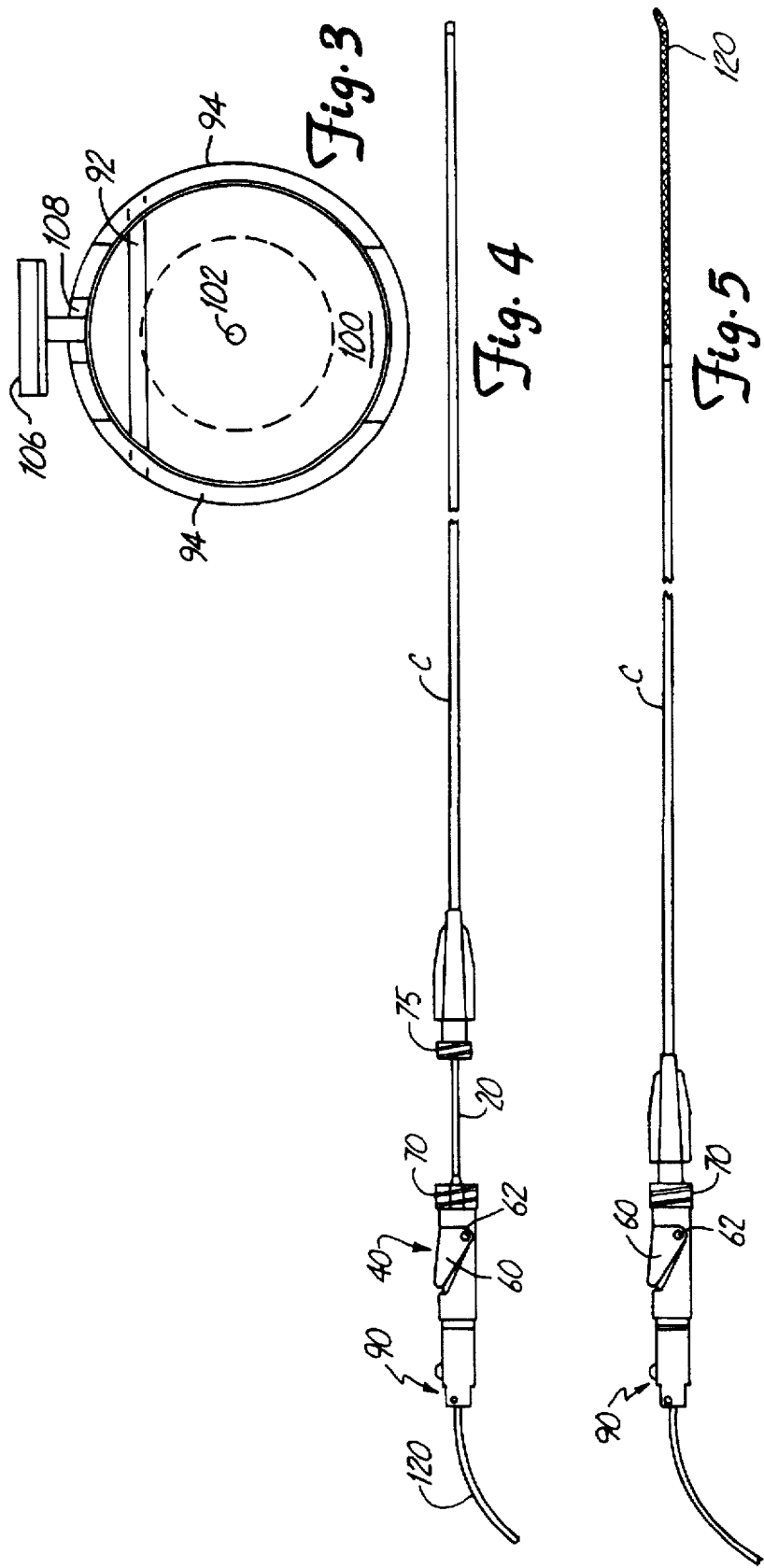

1

GUIDEWIRE STEERING HANDLE AND METHOD OF USING SAME

FIELD OF THE INVENTION

The present invention provides a steering handle for use in connection with medical guidewires, and has particular utility in procedures wherein both a guidewire and a catheter or other treatment device is necessary.

BACKGROUND OF THE INVENTION

In many medical procedures, minimally invasive procedures are used to treat various conditions without requiring surgery. In many of these instances, a treatment device is directed to the desired treatment site by means of a guidewire. The guidewire is typically guided through a patient's vessels, such as in the vascular system, to a position adjacent the desired treatment site. The treatment can then be performed with a catheter or the like. For example, a drug or embolization agent can be delivered through the catheter to the treatment site, or the catheter may include an inflatable angioplasty balloon to improve vessel patency. As another example, the treatment device can include a mechanical burr or the like which can be rotated to break down thrombi or atheroma in a blood vessel.

In some such procedures, the catheter or other treatment device can have difficulty "tracking", i.e. following along, the guidewire, to the treatment site. Poor tracking arises for several reasons. One such reason is that the catheter may not be stiff enough to follow the guidewire through a narrowing of the vessel, such as in the case of an atheroma in a blood vessel. In other cases, the catheter is actually too stiff and cannot follow the guidewire through a tortuous path without moving the distal portion of the guidewire from its carefully selected position.

Many users have attempted to solve one or both of these problems by modifying the catheters. In one such proposed solution, the catheter is made of a stiffer material to prevent it from kinking. In some instances, such catheters even include braided stainless steel in the wall of the catheter to improve its "pushability", i.e. the ability of an operator to urge the catheter distally without having it kink or buckle. If the catheter is sufficiently stiff and has suitable torsional stability, it may be possible to eliminate the guidewire altogether, with the catheter itself being steered through the patient's vessels to the treatment site. This, however, obviously will not solve the problem encountered where the catheter is too stiff to track a guidewire through a tortuous path because it makes the catheter even more stiff.

Another proposed solution for certain applications is to physically attach a length of a guidewire to the distal end of the catheter or other treatment device. This provides a guidewire extending through much of the length of the device, with the guidewire extending beyond the distal tip of the treatment device to permit the device to be steered with the guidewire. One example of such a "fixed wire" system is the Probe III "balloon-on-a-wire" angioplasty device, commercially available from C.R. Bard, Inc. of Ballerica, Mass., USA.

Fixed wire devices have certain advantages over conventional two-piece systems having a separate guidewire and catheter. For example, since the guidewire and the catheter are advanced together, there is no problem with tracking of the catheter over the guidewire. Furthermore, these devices are stiffer than either the guidewire or the catheter alone, combining the axial strength of both elements to improve pushability. Another benefit of fixed wire systems is that one can immediately determine whether the catheter being used can reach the treatment site—if the device is unable to progress through the vessel (e.g. it is blocked by a particularly narrow stenosis) one will discover this before the guidewire is painstakingly guided to a more distal site.

Fixed wire systems do have some disadvantages, though. Fixed wire devices can be a little more difficult to steer than conventional guidewires, making the process of guiding the wire through the patient's vessels more time consuming. Additionally, if the selected device is not properly selected, such as where an angioplasty balloon is too large to pass through the patient's vessel to the intended treatment site or is too small to complete the procedure, one cannot simply switch treatment devices. Instead, one must retract the entire device, wire and all, and start over again.

In conventional systems with two separate components, if the treatment device is found to be less than optimal, one can usually leave the guidewire in place and simply exchange treatment devices without losing the position of the guidewire. This can be particularly useful in some procedures where more than one treatment device is needed, such as in a multi-stage angioplasty where two or more differently sized balloons may be employed. With fixed wire systems, though, one must withdraw the first treatment device and guide the second treatment device all the way through the patient's vessel to the treatment site again.

When an operator directs a guidewire through a patient's system of vessels, he or she will ordinarily rely on a curvature of a distal length of the wire to help in this process. The length and radius of this curvature, as well as whether there will be one curve or several different curves, will frequently depend on a number of different factors, including the location of the treatment site, the age of the patient (which can affect the dimensions of the vessels), and the personal preferences of the operator. Many manufacturers manufacture and sell a number of different distal shapes for each size of guidewire, making production and inventory control difficult for the manufacturer and increasing inventory for hospitals and individual operators.

Most times, even if a guidewire is generally shaped properly, an operator will still tend to alter the shape somewhat to conform to his or her personal preferences in light of a particular patient's vascular anatomy or similar parameters. The shape of the wire can be altered in a number of different ways. Operator will commonly pinch the wire between the pad of a finger and the thumbnail of the same hand and then drag a length of the wire between the thumb and finger. This will tend to curve the wire, with the side which engages the pad of the finger being stretched longer than the side against the thumbnail. Operators also will frequently use a scalpel blade instead of a thumbnail, pinching the wire between the scalpel blade and the pad of a thumb, with the side engaging the thumb being elongated more than the side engaging the blade to produce a curve in the wire.

Although these manual methods of shaping the guidewire are acceptable, they are not very reproducible. In light of the fairly delicate natures of the wires commonly employed, the wire can be fairly sensitive to variations in pressure applied in the shaping process. Since the operator must simply guess how much force is being applied between a thumb and either another finger or a scalpel blade, the curve achieved from one time to the next can vary significantly.

In order to standardize the curvature of guidewires and the like, some inventors have proposed shaping devices which can be used instead of a thumbnail or a scalpel blade. For example, U.S. Pat. No. 4,716,757 (McGregor et al.) shows an apparatus that allows an operator to guide a guidewire through a sleeve, positioning the section of the guidewire to be bent on a hinge. By bending the sleeve about the hinge, the guidewire is said to be reproducibly bent.

In U.S. Pat. No. 5,277,231, Dostalek illustrates a complex wire stylet former. This former has a handle with four separate bending channels, each having a different radius of curvature, and a curved cover which engages the handle. When an operator desires to shape a wire stylet, he or she places the stylet in one of the four bending channels, positions the handle adjacent a pair of specially designed guide templates and aligns the stylet with the selected positions on the templates to achieve the desired curvature. The cover is then clamped down on the handle and the operator has to withdraw the stylet from the handle while keeping the stylet aligned with the selected template positions.

However, these devices can be inconvenient to use and the degree of precision offered by some of these devices, particularly the Dostalek stylet former, frequently is not necessary. It can also be somewhat inconvenient to have to keep a separate guidewire shaping device available, requiring hospitals to track another item or several additional items in their inventory and adding to the equipment needed in a fully stocked operating area.

SUMMARY OF THE INVENTION

The present invention provides a method of guiding a catheter and a guidewire using a selective fixed wire arrangement. In accordance with this method, a steering handle comprising a manually graspable body adapted to receive a length of the guidewire therethrough, a manually actuatable clamp for selectively gripping the guidewire and a fitting is provided. The operator places a length of the guidewire through the lumen of the catheter and places a segment of the guidewire disposed proximally of the catheter in the body of the steering handle and attaches the handle to the guidewire with the clamp. The operator introduces the catheter and the guidewire into a patient's vessel (e.g. a vessel of a patient's vascular system) and attaches the fitting of the handle to a fitting provided adjacent the proximal end of the catheter and manually grasps the handle and urges the guidewire and the catheter together as a unit along the vessel.

In another embodiment, the invention provides a steering handle for use by an operator. This steering handle may comprise a manually graspable body, with the body being adapted to receive a length of a guidewire therewithin, and a fitting carried adjacent the distal end of the housing for attachment to a proximal end of a catheter. It also can include a clamp positioned within a cavity in the body and generally aligned with the guidewire channel, the clamp being moveable between a first position wherein it grasps the guidewire and a second position wherein the guidewire is free to move with respect to the clamp, the clamp in its first position sealingly abutting against a collar in the body to provide a substantially fluid-tight seal, and a spring or the like biasing the clamp toward the first position.

BRIEF DESCRIPTION OF THE DRAWINGS

FIG. 1 is a schematic, cross sectional view of a steering handle in accordance with one embodiment of the invention;

FIG. 2 is a schematic, cross sectional view of the steering handle of FIG. 1 with a guidewire received therein;

FIG. 3 is an end elevational view of the steering handle of FIG. 1;

FIG. 4 is a side elevational view of a steering handle in accordance with an embodiment of the invention, a guidewire and a treatment device, with the steering handle being spaced from the treatment device;

FIG. 5 is a side elevational view of the steering handle, guidewire and treatment device of FIG. 3 with the steering handle attached to the treatment device;

DETAILED DESCRIPTION OF PREFERRED EMBODIMENTS

Figure 6A:
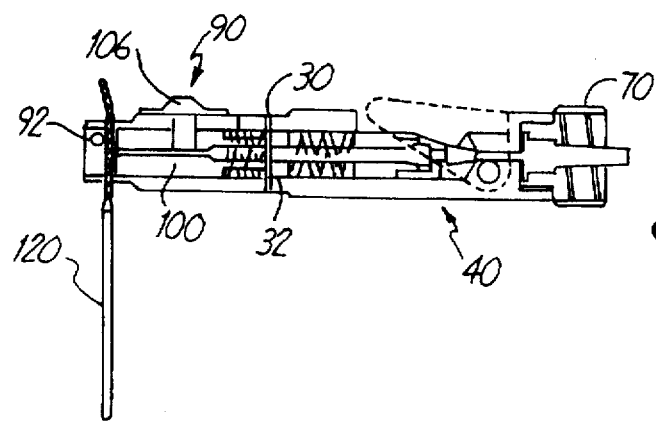
FIGS. 6A–6C are schematic cross sectional views schematically illustrating use of a steering handle of an embodiment of the invention to shape a portion of a guidewire.

One preferred embodiment of a steering handle 10 is shown in the attached drawings. Turning first to FIGS. 1–3, the steering handle 10 generally comprises a manually graspable body 20 which may take the form of an elongate, generally cylindrical wall 22 defining an internal cavity 24 within the body. The body of the embodiment shown in FIGS. 1–7 is functionally divided into a steering segment 40 and a guidewire shaper segment 90.

The wall 22 of the body may be integrally formed of a single element which extends along the length of the body (as shown) or it may be formed of two separate elements bonded together, with the wall comprising a steering length extending along the steering segment 40 and a shaping length extending along the guidewire shaper segment 90. For reasons which are detailed below, a pair of posts 30 (only one is visible in the cross sectional views of FIGS. 1 and 2) may be positioned between the two segments 40, 90 of the body 20 and a spring stop 32 may abut against the post.

The steering segment 40 of the body includes a clamp 130 carried within the cavity 24. The clamp may be of any design which can adequately clamp the steering handle 10 onto a guidewire 120 to permit the guidewire to be manipulated by an operator grasping the handle. This gripping force is desirably at least about 1 pound to maintain a good connection between the handle 10 and the wire 120, with a gripping force of 2.75–4.0 pounds, and more desirably greater than 3.0 pounds, being preferred. In a preferred embodiment, the clamp 130 comprises a collet which will narrow in inner diameter when axially compressed and tend to expand to a predetermined inner diameter when not under such compression. Such collets are well known devices and need not be discussed in any further detail here.

However, one particularly preferred embodiment of the clamp 130 is illustrated in the attached drawings. In this embodiment, best seen in FIG. 7, the clamp 130 comprises an elongate, generally tubular member having a lumen 131 extending therethrough so that a guidewire 120 may pass through the clamp. The clamp comprises three main segments—a distal segment 132, an intermediate segment 138 and a proximal segment 140. The distal segment 132 is desirably generally frustoconical so that when it engages against the tapering distal wall 46 of the steering segment 40 (described below) the distal segment will be urged closed.

The intermediate segment 138 of the clamp 130 desirably has a smaller outer diameter than the proximal end of the distal segment. This will define a proximally facing shoulder 134 for engaging the actuator 150, as described below. The proximal segment 140 in the illustrated embodiment comprises an elongate tube, similar to a conventional hypotube. The distal end of the proximal segment 140 desirably has a larger outer diameter than the intermediate segment 138 to present a distally facing shoulder 142 for engagement by the actuator 150.

Figure 7:
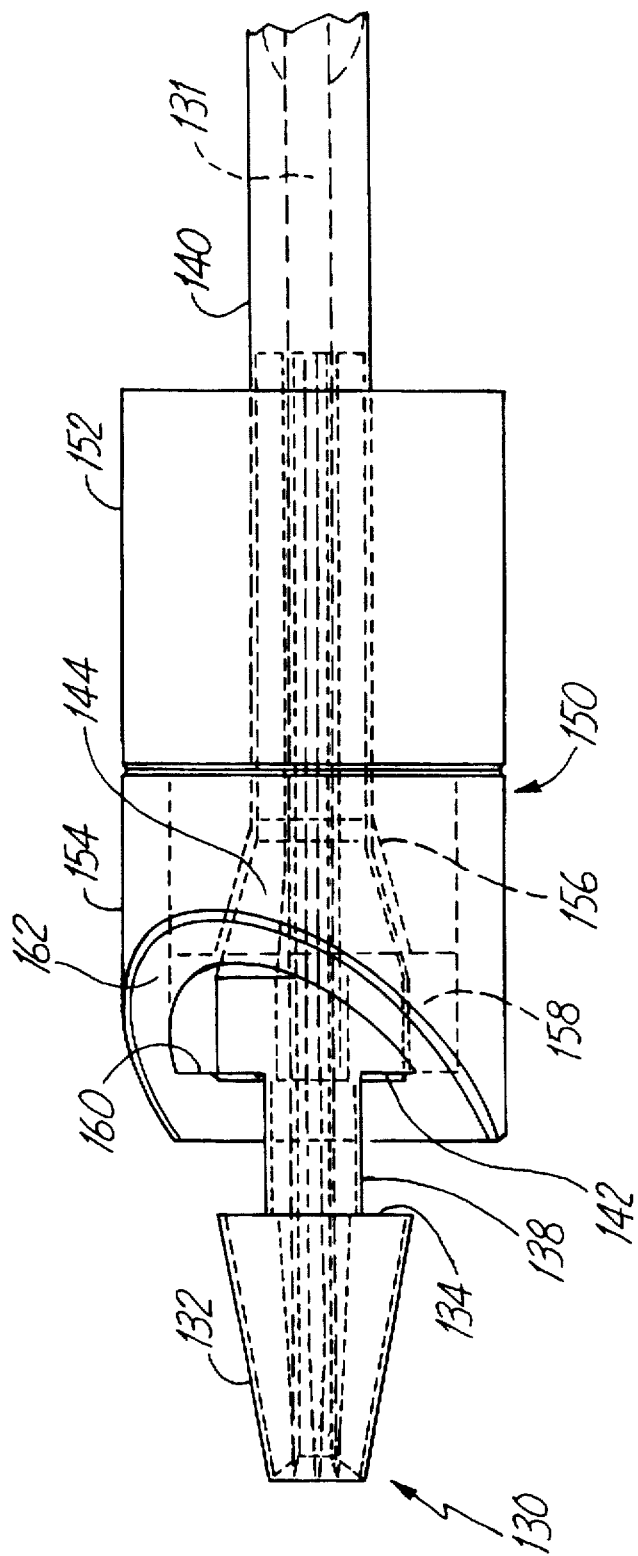
FIG. 7 is a side isolation view of a clamp mechanism for use in connection with the steering handle of FIG. 1.

Although the proximal segment may have a constant outer diameter along its length, the embodiment shown in the drawings has a smaller diameter along much of its length, but includes a taper 144 nearer the distal end to provide a smooth transition to the larger diameter at the distal shoulder 142. If so desired, the lumen may taper outwardly in a proximal direction, as shown in FIG. 7, to assist in inserting the distal end of a guidewire into the proximal end of the clamp.

The clamp 130 includes a plurality of slots (shown in phantom in FIG. 7) which extend along a portion of the length of the clamp. In the embodiment shown, the slots extend from the distal end of the clamp to a position on the proximal half of the proximal segment. These slots are desirably oriented generally radially outwardly from the lumen 131 and pass through the entire thickness of the wall of the clamp. This divides the clamp into a number of independent fingers all attached to the proximal segment 140.

In a relaxed state, the fingers are desirably spaced slightly away from one another, either by flexing radially outwardly from their connection to the proximal segment or by being generally parallel to the axis with a wider slot between elements. When the distal segment 132 engages the distal wall 46 of the handle, as described below, this will tend to urge the fingers radially inwardly into engagement with one another or, if a guidewire is present in the lumen 131, into engagement with the guidewire.

As best seen in FIGS. 1 and 2, the steering segment 40 also includes means for biasing the clamp toward its closed position wherein it clamps down against a guidewire. In FIGS. 1 and 2, this biasing means is typified by a spring 44 and a distal wall 46 of the body. The spring in this design is a compression spring which urges distally against the clamp 130 in a manner described below, urging the clamp forwardly against the distal wall 46. As noted above, this axial compression will cause the collet to restrict, effectively grasping any guidewire extending through the body. In order to ensure proper closure of the clamp 130 about a guidewire, it is preferred that this distal wall 46 taper inwardly in a distal direction to present a generally frustoconical shape, as shown.

When the clamp 130 is in this distal position and engaged against the distal wall 46 (as shown in FIG. 1), a generally fluid-tight seal is formed between the clamp distal segment 132 and the wall of the clamp desirably generally sealingly clamps against the guidewire. When a catheter is attached to the fitting 70, as explained below, the clamp can serve to limit, and perhaps even effectively prevent, the backflow of blood through the steering handle during use.

Although proximal movement of the spring 44 may be limited in any suitable way, the illustrated embodiment employs a pair of posts 30 which define chords through the cylindrical body spaced away from the axis of the body. The space between the posts should be large enough to permit a guidewire to pass between the posts unhindered, but should not allow the spring 44 to pass therethrough. In order to further prevent the spring from passing between the posts, a generally annular spring stop 32 can be positioned between the spring 44 and the posts 30, with the stop 32 having a central orifice large enough to allow a guidewire to slide therein.

The spring 44 can abut directly against the proximal end of the clamp, but the illustrated embodiment of the invention includes an actuator 150 disposed between the spring and the clamp. As best seen in FIG. 7, this actuator is sized to permit it to slide generally axially within the cavity 24 of the body and includes a channel 151 extending generally along its axis to receive a portion of the proximal segment 140 of the clamp therethrough. The proximal segment 140 of the clamp may extend proximally beyond the proximal end of the actuator, with the exposed length of the proximal segment being received within the lumen of the spring 44 and sliding therewithin.

The actuator 150 can be integrally formed, such as of a single piece of a plastic or metal material. In order to make fabrication easier, though, the embodiment shown in the drawings has an actuator formed of separate proximal 152 and distal 154 pieces. The actuator also desirably includes a generally frustoconical taper 156 therein sized and shaped to fairly closely receive the taper 144 of the proximal segment. The spring 44 will urge the actuator forwardly and this taper 144 and recess 156 arrangement will help ensure reliable positive engagement between the actuator and the clamp.

The actuator also includes a recess 158 within which a distal portion of the proximal segment is received. A rearwardly facing lip 160 is provided at the distal end of this recess and it extends generally upwardly from the bottom of the actuator (in the orientation shown in FIGS. 1 and 2). When the actuator is urged distally, as described below, this lip 160 will engage the distally facing shoulder 142 of the clamp's proximal segment and draw the clamp 130 distally with the actuator, as illustrated in FIG. 2.

The steering segment 40 of the body also includes a manually actuatable arm 60 which can be used to move the actuator 150 along the body and actuate the clamp 130. If so desired, the arm can simply be directly attached to the actuator and slide generally axially within a slot in the wall 22 of the steering segment, much like the button 106 of the shaping segment 90 described below.

In the embodiment of FIGS. 1 and 2, though, the arm is attached to the wall 22 of the body by means of a pivot pin 62. By pivoting the arm about this pivot pin, an operator can move the actuator 150, and hence move the attached clamp 130 between a first position wherein the clamp grasps the guidewire 120 and a second position wherein the guidewire is free to move with respect to the clamp (illustrated in FIG. 2). The arm may take the form of an arcuate shell having a diameter about the same as the diameter of the body adjacent its attachment thereto, as shown.

In one preferred embodiment, the distal end of the actuator may be provided with an angled, distally facing upper face 162 (FIG. 7). The arm 60 includes a projection 64 which extends inwardly from the inner surface of the arm and this projection desirably has an angled, proximally facing surface which may slide along the upper face 162 of the actuator.

When there is no pressure on the arm, the biasing force of the spring 44 against the actuator 150 pushes distally against the projection 64 of the arm. This projection can slide generally upwardly along the upper face 162 of the actuator, pivoting the arm upwardly so that it extends beyond the body, as shown in FIG. 1. When an operator depresses the arm, such as by squeezing it down with a thumb or finger, the arm's projection 64 will act against the upper face 162 of the actuator. The projection 64 will then slide downwardly along the face 162 and urge the actuator 150 proximally against the force of the spring. As best seen in FIG. 2, this will move the distal segment 132 of the clamp proximally away from the distal wall 46, allowing the clamp to open and permit the guidewire 120 to move with respect to the clamp. When the arm is released by the operator, the spring 44 will urge it back into the position shown in FIG. 1.

The steering handle also includes a fitting 70 which is adapted to be attached to the proximal end of a treatment device, such as a catheter. (In the examples below, the discussion will center on a catheter as the treatment device, but it should be understood that any suitable treatment device, such as a balloon catheter, an atherectomy device, a thrombectomy device or the like, could be used instead of the catheter.) For example, most catheters made and sold in the United States are provided with a standard-sized male Luer fitting on their proximal end and the fitting 70 may comprise a female Luer fitting, as shown in the drawings, sized to mate with the standard male Luer fitting (75 in FIG. 4).

As noted above, a body 20 of a steering handle 10 of the invention may also include a shaper segment 90, which provides a guidewire shaper. It has been found to be particularly convenient to have a device for shaping a guidewire as part of the present steering handle. It is to be understood, though, that a steering handle need not include both a steering segment 40 and a guidewire shaper segment 90 as either of these portions of the illustrated steering handle 10 can provide certain benefits to the user without the other portion of the handle. This is particularly true of the steering segment 40 of the steering handle in that it provides a remarkably superior steering system, as described below, even without the guidewire shaper segment.

The steering handle 10 shown in FIGS. 1–3 does include a guidewire shaper segment 90. This guidewire shaper can be attached to the steering segment 40 of the body in any useful configuration, but in a preferred embodiment, the guidewire shaper segment 90 of the body is axially aligned with the steering segment 40 of the body and the wall 22 of the body extends along both of these segments. The cavity 24 of the body extends through the guidewire shaper segment, with the pair of posts 30 noted above functionally defining the division of these two segments of the body.

The guidewire shaper 90 may generally comprise a shaping piston 100 and a shaping pin 92. The shaping piston in this embodiment has a guidewire channel 102 extending therethrough generally along it axis to permit a guidewire 120 to pass through the piston, as illustrated in FIG. 2. The wall 22 of the body has a slot extending through a proximal length of thereof, defining a pair of spaced-apart, arcuate pillars 94 (best seen in FIG. 3). One end of the shaping pin is attached to one pillar and the pin is attached at its other end to the other pillar. The pin is desirably oriented in a plane perpendicular to the axis of the shaping handle, but the pin is positioned so that it is disposed away from that axis, defining a chord across the circular end of the handle as shown in FIG. 3. This permits a guidewire to pass through the guidewire channel 102 of the piston without interference from the pin.

The guidewire shaper also includes a spring 96 or the like which serves to bias the piston 100 toward abutment with the pin 92. The spring 96 abuts the posts 30, mentioned above, at its distal end to prevent further travel of the spring within the cavity. The spring will, therefore, exert a substantially constant biasing force against the piston when the spring is in its relaxed state shown in FIGS. 1 and 2. The piston may include a distal portion 104 having a reduced outer diameter so that it may be slidingly received within the lumen of the spring 96. The change in outer diameter of the piston is desirably relatively sharp so that the piston defines a distally facing shoulder against which the proximal end of the spring may push.

The shaping piston 100 should be manually actuatable by an operator so that it can be moved away from the shaping pin 92 to permit a guidewire to be inserted therebetween, as outlined below. In order to make it easier for an operator to use the guidewire shaper, a manually engagable button 106 may be provided, with the button extending laterally through a track 108 in the wall of the body. By urging the button 106 distally, e.g. with a thumb, the operator can readily move the piston distally against the biasing force of the spring 96.

As noted above, the present invention also provides a method of guiding a guidewire and a catheter. FIGS. 4 and 5 schematically illustrate certain aspects of such a method using the steering handle 10 outlined above.

In accordance with a first method of the invention, the operator is provided with a steering handle (e.g. steering handle 10) having a manually graspable body (e.g. body 20) which can receive a length of guidewire therethrough, a clamp for gripping the guidewire and a fitting. Although the steering handle 10 shown in FIGS. 4 and 5 is the same as that shown in FIGS. 1–3, it should be understood that the design of the steering handle can be changed significantly from that illustrated in FIGS. 1–6 without adversely affecting the ability of an operator to carry out the method. For example, the guidewire shaper 90 could be entirely omitted from the steering handle without preventing an operator from carrying out many embodiments of the present method.

The operator in performing this method places a length of the guidewire through the lumen of a catheter C (or other treatment device), places a length of the guidewire through the cavity 24 of the steering handle, and introduces both the guidewire and the catheter to a patient's vessel. At some point in the operation, the fitting of the steering handle is attached to the fitting 75 carried by the catheter adjacent its proximal end. The operator can manually grasp the steering handle and urge the guidewire and catheter, both of which are connected to the steering handle, together as a unit along the patient's vessel.

These steps can be performed in any order, depending on such factors as the operator's preference and the specific procedure being preformed. Most commonly, perhaps, the operator will first insert the guidewire into the patient's vessel (e.g. a vein or artery) then slide the catheter over the guidewire and into the patient's vessel, with a proximal length of the guidewire extending proximally beyond the proximal end of the catheter. A length of the guidewire disposed proximally of the catheter would then be placed in the steering handle 10 by manually depressing the arm 60 sufficiently to allow the guidewire to pass freely through the clamp 130 and continuing to hold the arm down while guiding the guidewire through the cavity 24, preferably until the wire passes through the guidewire channel 102 of the shaping piston and extends proximally of the handle, as shown in FIG. 4.

The fitting 70 of the steering handle can be attached to the mating fitting 75 of the catheter in any suitable manner. In the embodiments shown wherein the mating fittings 70, 75 are Luer fittings, this can be accomplished simply by screwing the mating parts together. This connection can be made at any point in the operation. Although these elements could be connected outside the patient's body and introduced into the patient's vessel as a unit, more commonly operators will likely choose to introduce the guidewire 120 and catheter C as separate components and attach the catheter to the steering handle 10 later.

If so desired, an operator can connect the handle to the catheter shortly after the catheter and guidewire are introduced into the patient's vascular system, i.e. before these separate elements are advanced a significant distance down the length of the vessel. In one preferred embodiment of the present method, however, the guidewire is steered independently of the catheter along the patient's vessel and the catheter is separately urged distally to track along the guidewire. When an operator chooses to guide the guidewire and catheter independently of one another, in most circumstances the operator will allow the guidewire to extend distally beyond the distal end of the catheter. This permits the operator to take advantage of the superior torque properties of most guidewires in accurately steering the guidewire and the catheter can simply follow along the path already defined by the guidewire.

Similarly, when the operator attaches the steering handle to the catheter, he or she will typically allow the guidewire to extend beyond the distal tip of the catheter. This guidewire provides a more readily articulatable part of the combined system to be at the leading edge of the device when it is being steered into place.

In accordance with a further embodiment of the present method, the operator exchanges the original catheter for another catheter or some other treatment device. In the standard catheter exchange process, an extension wire will be attached to the proximal end of the guidewire and the operator will hold onto either the guidewire or the extension wire at all times while retracting the catheter behind the proximal end of the guidewire. As the steering handle is likely larger than the lumen of the catheter, the operator probably cannot retract the catheter over the steering handle. Accordingly, the operator will typically have to either remove the steering handle from the guidewire and then retract the catheter, or hold down the arm 60 of the handle to permit it to slide off the guidewire while leaving the fittings 70, 75 attached, withdrawing the catheter using the steering handle to grasp the catheter.

In another method of effecting catheter exchange, the operator will withdraw a length of catheter from the patient's body, cut a proximal length of the catheter, and remove that proximal length from the guidewire. That process is repeated until the catheter is completely removed from the guidewire in pieces. (This process is described in U.S. Pat. No. 5,368,561, the teachings of which are incorporated herein by reference.) In order to accomplish this process, the operator will have to remove the steering handle from the guidewire to permit the segments of the catheter to be removed from the wire.

Regardless of what catheter exchange technique is chosen, though, the operator will typically have to remove the handle 10 from the guidewire 120 to permit the new catheter to be introduced over the guidewire. Once the catheter is advanced into the patient's vessel a sufficient distance to expose the proximal end of the guidewire, the steering handle can once again be introduced over the guidewire and attached to either the guidewire or the catheter until the operator decides to attach the wire and catheter to the handle and urge the wire and catheter along the patient's vessel as a unit.

The present invention permits an ordinary guidewire 120 and catheter C to be used in their normal fashion, wherein they are guided independently, and to be guided as a unit. In essence, the present invention provides all of the benefits of a "fixed wire" system while allowing the operator to avoid many of the pitfalls of such systems by giving him or her the flexibility to convert the system back to a standard, independent wire system at any time simply by disconnecting the steering handle from the catheter.

The point at which the operator chooses to connect the steering handle to the catheter will vary from one procedure to the next, but it may be done when the operator finds he or she needs some additional "pushability" or when approaching a narrow portion of the vessel. For example, when an operator is attempting to guide the guidewire along a tortuous path and finds that the guidewire is tending to kink, the operator can attach the catheter to the steering handle. Then when the operator urges the steering handle distally, the added stiffness of the catheter may allow the operator to more effectively push the wire.

As another example, when the operator is attempting to traverse a narrow stenosis of a vascular vessel and is unsure whether the selected catheter or other treatment device is of an appropriate size, he can attach the handle to the catheter and urge the wire and catheter distally as a unit. This permits the operator to determine whether the catheter will pass through the treatment site. If the operator cannot urge the catheter through the stenosis without undue pressure, he can exchange the catheter for a smaller catheter or for a different type of treatment device altogether. Unlike a standard fixed wire system, the present steering handle 10 permits the operator to keep the guidewire in place and simply track the new catheter or other device over the wire until the stenosis is reached again, eliminating the need to manually guide a new fixed wire system all the way back to the previous position.

Figure 6B:
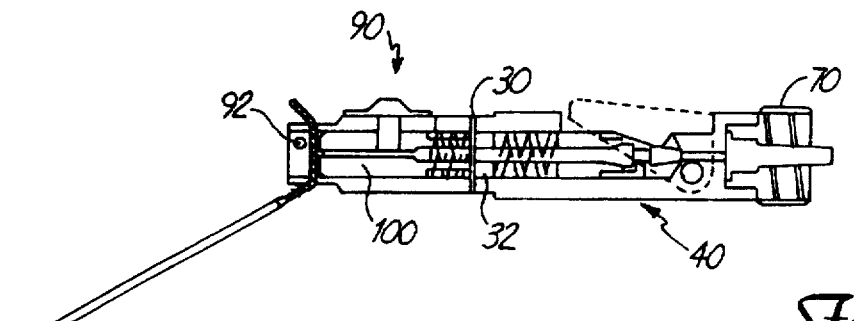
Figure 6C:
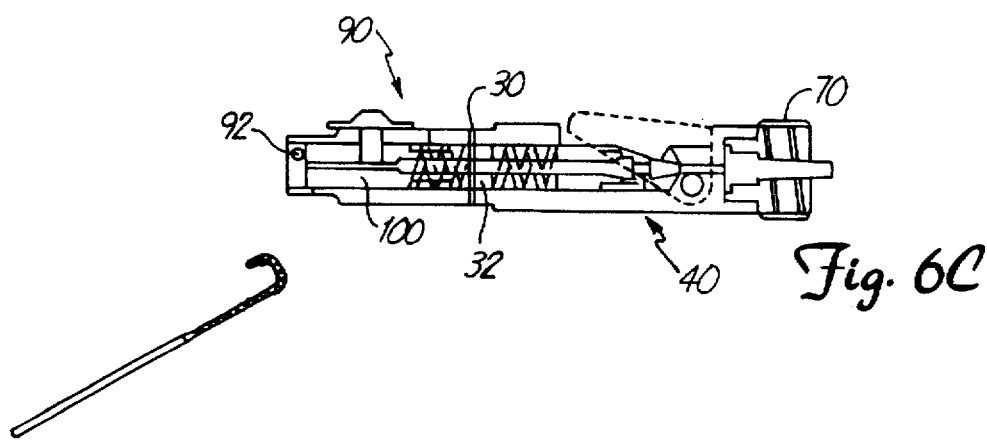

In accordance with a further embodiment of the present invention, a distal length of the guidewire is shaped with the steering handle's guidewire shaper 90 before the wire is introduced into the patient's body. FIGS. 6A–6C schematically illustrate the process of shaping the guidewire.

Turning first to FIG. 6A, the operator places the guidewire between the shaping piston 100 and the shaping pin 92. As mentioned above, this can be accomplished by urging the piston distally with the button 106 to create a gap between the pin and the proximal end of the piston. The guidewire can then be placed in the gap, with a distal length of the wire which the operator wants to shape extending beyond the pin, as shown. When the operator releases the piston, the spring 96 will urge the piston against the guidewire, pinching the guidewire between the piston and the pin with a predetermined force.

The operator can the begin retracting the guidewire proximally, orienting the proximal portion of the wire at an angle with respect to the end of the piston, as shown in FIG. 6B. When the guidewire is fully retraced from the guidewire shaper 90 in this fashion, the length of wire drawn between the piston and pin will be curved, with the side of the wire engaged against the pin being shorter than the opposite side, as illustrated in FIG. 6C.

The resulting degree of curvature in the wire is determined by a number factors, including the properties of the guidewire being shaped, the pressure of the piston and pin against the wire, and the angle at which the operator retracts the wire. As the force of the piston and pin against the wire is predetermined by the spring 96, for a given guidewire, the degree of curvature will be dictated by the angle at which the wire is withdrawn. Accordingly, if an operator wants a sharper curve, he can increase the angle between the wire and the piston's end; if a more gentle curve is wanted, the operator can decrease that angle. Once the guidewire has been curved as desired, the operator can then proceed to use the same steering handle to steer the guidewire as detailed above.

While a preferred embodiment of the present invention has been described, it should be understood that various changes, adaptations and modifications may be made therein without departing from the spirit of the invention and the scope of the appended claims.

What is claimed is:

1. A method of guiding a catheter and a guidewire comprising the steps of:
   a. providing a steering handle comprising a manually graspable body adapted to receive a length of the guidewire therethrough, a manually actuatable clamp for selectively gripping the guidewire, a fitting, and a shaping pin;
   b. shaping a distal length of the guidewire with the shaping pin of the steering handle;
   c. placing a length of the guidewire through the lumen of the catheter;
   d. placing a segment of the guidewire in the body of the steering handle and attaching the handle to the guidewire with the clamp;
   e. introducing the catheter and the guidewire into a patient's vessel;
   f. attaching the fitting of the handle to a fitting provided adjacent the proximal end of the catheter; and
   g. manually grasping the handle and urging the guidewire and the catheter together as a unit along the vessel.

2. The method of claim 1 wherein the step of shaping the guidewire comprises pinching the guidewire between a shaping piston and the shaping pin with a predetermined force, and retracting the guidewire at an angle with respect to the shaping pin.

3. The method of claim 2 wherein the step of placing a segment of the guidewire in the body of the steering handle comprises passing a length of the guidewire through the shaping piston.

4. The method of claim 2 wherein the step of placing a segment of the guidewire in the body of the steering handle comprises passing a length of the guidewire through the shaping piston.

5. The method of claim 1 wherein the step of shaping the guidewire comprises pinching the guidewire between a shaping piston and the shaping pin with a predetermined force, and retracting the guidewire at an angle with respect to the shaping pin.

6. A method of guiding a medical catheter and a guidewire comprising the steps of:
   a. providing a steering handle comprising a manually graspable body adapted to receive a length of the guidewire therethrough, a manually actuatable clamp for selectively gripping the guidewire, a fitting, and a shaping mechanism;
   b. placing a length of the guidewire through a lumen of the catheter;
   c. shaping a distal length of the guidewire with the shaping mechanism of the steering handle;
   d. subsequently placing a segment of the guidewire disposed proximally of the catheter in the body of the steering handle and attaching the handle to the guidewire with the clamp;
   e. introducing the catheter and the guidewire into a patient's vessel;
   f. steering the guidewire independently of the catheter along the vessel and separately urging the catheter distally to track along the guidewire;
   g. thereafter attaching the fitting of the handle to a fitting provided adjacent the proximal end of the catheter; and
   h. manually grasping the handle and urging the guidewire and the catheter together as a unit along the vessel.

* * * * *